United States Patent [19]

Glabiszewski

[11] 4,089,072
[45] May 16, 1978

[54] PROSTHETIC APPLIANCE

[75] Inventor: Richard Glabiszewski, Duderstadt, Germany

[73] Assignee: Otto Bock Orthopädische Industrie K.G., Duderstadt, Germany

[21] Appl. No.: 704,782

[22] Filed: Jul. 13, 1976

[30] Foreign Application Priority Data

Jul. 18, 1975 Germany .................. 7522922[U]

[51] Int. Cl.² ............................ A61F 1/04; A61F 1/08; A61F 1/06

[52] U.S. Cl. ................................................. 3/30; 3/2; 3/6; 3/12

[58] Field of Search ........................................ 3/30–35, 3/6–7, 12, 21, 2

[56] References Cited

U.S. PATENT DOCUMENTS 3,890,650  6/1975  Prahl .............................................. 3/7
3,953,900  5/1976  Thompson .................................... 3/2

FOREIGN PATENT DOCUMENTS 117,497  9/1943  Australia ....................................... 3/2
813,191  9/1951  Germany ...................................... 3/7

Primary Examiner—Ronald L. Frinks
Attorney, Agent, or Firm—Michael J. Striker

[57] ABSTRACT

A prosthetic appliance comprises a supporting part and an extremity-shaped part which is articulated to the end portion of the supporting part. A sheath surrounds the supporting part, and a cup-shaped element is permanently connected to the sheath and detachably connected to the extremity-shaped part and bounds a compartment in which the end portion of the supporting part is received with freedom of movement relative to the cup-shaped element. The cup-shaped element may be snugly received in a depression of the second part and circumferentially surrounded by a rim of the latter, being flush with an end face thereof.

7 Claims, 2 Drawing Figures

PROSTHETIC APPLIANCE

BACKGROUND OF THE INVENTION

The present invention relates to a prosthetic appliance, and particularly to a prosthetic appliance intended to replace an amputated extremity or limb of a human body.

There are already known various prosthetic appliances of the type here under consideration, which are used for replacement of severed human feet or hands. The present invention will be described as employed in a prosthetic appliance which takes the place of a severed foot; however, it is to be understood that a similar concept may also be used in a prosthetic appliance for replacing an amputated hand.

Usually, the conventional prosthetic appliances include a supporting part which is connected to the body of the user, a foot or other extremity part which is connected to the free end portion of the supporting part, and a sheath made of an elastically yieldable material, preferably foamed rubber or synthetic plastic material which surrounds at least the supporting part of the appliance and gives the same an aesthetically pleasing appearance. Inasmuch as the primary purpose for the sheath, besides protecting the supporting element from detrimental influences of the environment, is to improve the appearance of the prosthetic appliance, it will be hereafter called a cosmetic sheath.

In the conventional prosthetic appliances, the extremity-shaped part is made of a rigid material, such as wood, synthetic plastic material or the like, and the cosmetic sheath, as already mentioned above, is made of a resiliently yieldable material. In order to give the prosthetic appliance a compact outlook, it is necessary to connect the cosmetic sheath with the foot or other extremity part. This, however, brings about a variety of problems.

First of all, only certain types of connecting procedures which do not impair the appearance of the prosthetic appliance can be used for connecting the cosmetic sheath to the extremity-shaped part. Such procedures primarily involve gluing or welding, particularly thermal welding. These procedures, as is well known, result in permanent bonds which are not easy to dissociate without damaging or destroying one of the connected components.

Another problem results from the fact that some of the various components of the prosthetic appliance are connected with one another using adjustable connecting elements. The adjustment of the position of the various components relative to one another may itself result in impairment of the appearance of the resiliently yieldable cosmetic sheath. However, more importantly, after the original adjustment, any subsequent adjustment of the positions of the various components relative to one another requires that access be obtained to the components the positions of which are to be adjusted. Most of the time, such access may be had only upon removal or partial removal of the cosmetic sheath which, in the event of a permanent bond between the cosmetic sheath and the extremity-shaped part, necessitates at least a partial cutting up of the bond between the cosmetic sheath and the extremity-shaped part which is glued or welded thereto, or of the cosmetic sheath proper. When the former approach is taken, it may be very difficult to reestablish a permanent bond between the cosmetic sheath and the extremity-shaped part. In the latter event, the damaged cosmetic sheath must be restored to its original appearance, to the extent possible, by gluing or otherwise connecting the cut-up sections of the cosmetic sheath. This, of course, is very difficult to do, particularly when it is desired, as it always is, to restore the aesthetically pleasing intact appearance of the sheath.

In order to avoid this difficulty, it has been already proposed to connect the cosmetic sheath to the extremity-shaped part by inserting the end portion of the cosmetic sheath into a recess formed in the end face of the extremity-shaped part. However, experience with this approach has shown that such a connection is not particularly reliable, especially because of the fact that only frictional engagement of the end portion of the cosmetic sheath with the surfaces bounding the recess is obtained. Also, the outward appearance of the prosthetic device leaves much to be desired inasmuch as formation of visible seams is unavoidable when this approach is taken.

An attempt has already been made to avoid these drawbacks which are inherent to the solution in which the cosmetic sheath is directly connected to the extremity-shaped part of the prosthetic appliance either by an end-to-end gluing or welding, or by inserting the end portion of the cosmetic sheath into a recess of the extremity-shaped part. In this approach, which has been heretofore used only in prosthetic appliances in which there is no relative movement between the various components, a connecting element is interposed between the cosmetic sheath and the extremity-shaped part, such connecting element being of a plate-shaped configuration and being permanently connected to the cosmetic sheath. In this prior-art appliance, the connecting element has an exposed surface having at least two receiving recesses which extend normal to the exposed surface, opening thereon and leading into the plate-shaped connecting element, and the extremity-shaped part, such as a foot part, has an equal number of pins which are clampingly received within the corresponding recesses of the connecting element. In addition to the recesses, the plate-shaped connecting element is also provided with a central opening through which an end portion of a supporting element extends from the space surrounded by the cosmetic sheath toward the foot-shaped part.

In this prior-art appliance, the connection between the cosmetic sheath, and particularly between the plate-shaped connecting element which is permanently connected thereto, and the extremity-shaped part, can be established in a very simple manner in that the connecting element is aligned with the extremity-shaped part so that the pins of the extremity-shaped part are brought into registry with the recesses of the connecting element, whereupon the sheath or the connecting element is pressed against the extremity-shaped part to thereby obtain a clamping connection between the pins and the complementary recesses. Such connection can just as easily be discontinued by pulling the connecting element away from the extremity-shaped part. In view of the fact that the connecting element can be so shaped as to exactly correspond to the contour of the connecting surface of the extremity-shaped part of the prosthetic appliance, it is assured that, no matter now many times the connection between the cosmetic sheath and the extremity-shaped part is established and discontinued, the outer surfaces of the cosmetic sheath, the connecting element and the extremity-shaped part will always smoothly and gradually merge with one another without formation of any perceivable seams. It will be appreciated that, in this prior-art prosthetic appliance, the connection of the cosmetic sheath or of the connecting element permanently attached thereto with the extremity-shaped part of the prosthetic device can be arbitrarily often discontinued and reestablished without any damage to such connection or to the cosmetic sheath. In addition thereto, the fact that the connecting element is of a plate-shaped configuration and is permanently connected to the cosmetic sheath significantly contributes to reinforcing and stabilizing the cosmetic sheath and particularly the free end portion thereof, which is a very important consideration in view of the fact that the cosmetic sheath is usually made of a comparably weak or resiliently yieldable material, such as a foamed synthetic plastic material. Moreover, the pin-and-recess connection of the connecting elements with the extremity-shaped part assures that the cosmetic sheath reassumes its original position after each reassembly of the extremity-shaped part with the remainder of the prosthetic appliance.

It may be seen that the immediately above described prior-art prosthetic appliance has a number of advantages, particularly where the connection of the cosmetic sheath with the extremity-shaped part is concerned. However, as already previously mentioned, this approach does not readily lend itself for use in a prosthetic appliance in which the various components are articulated to one another, particularly in an appliance in which the extremity-shaped part is pivotally connected to the supporting part. Such articulated prosthetic appliances are also very well known and usually they include a tilting element which is pivotally supported on the extremity-shaped part and to which a tubular element of the supporting part, as well as the cosmetic sheath, are connected. This solution has a very important disadvantage in that, as the tilting element is angularly displaced relative to the extremity-shaped part, the cosmetic sheath which is connected to the tilting element is deformed, which results in an impairment of aesthetic appearance of the prosthetic appliance which, in most instances, is unacceptable to the user of the prosthetic appliance. Various solutions to this problem have already been attempted; however, such solutions are either very complex and thus impractical, or do not result in any significant improvement of the appearance of the prosthetic appliance during the use thereof.

SUMMARY OF THE INVENTION

Accordingly, it is a general object of the present invention to avoid the disadvantages of the prior art.

More particularly, it is an object of the present invention to provide a prosthetic appliance which is not possessed of the disadvantages of the prior-art prosthetic appliances.

It is a further object of the present invention to provide a prosthetic appliance which is simple in construction and reliable in operation.

A concomitant object of the present invention is to provide a prosthetic appliance of the articulated type in which the appliance has an aesthetically pleasing appearance regardless of the relative position of the various components thereof.

Yet another object of the present invention is to provide a prosthetic appliance in which the relative movement of the various components can be conducted without interference.

In pursuance of these objects and others which will become apparent hereafter, one feature of the present invention resides, briefly stated, in a prosthetic appliance, in a combination which comprises a supporting elongated first part which has an end portion; an extremity-shaped part second part which is articulated to the end portion of the first part; a sheath which surrounds at least a portion of the first part; and means for connecting the sheath to the second part, including a cup-shaped element which is permanently connected to the sheath and detachably connected to the second part, such cup-shaped element bounding a compartment in which the end portion of the first part is received with freedom of movement relative to the cup-shaped element. Preferably, the second part is of a rigid material, such as wood or synthetic plastic material, while the sheath is of a resiliently yieldable material, particularly foam rubber or foamed plastic material. The first part may include a tubular element, and a tilting element which is separate from and rigidly connected to the tubular element and which constitutes the end portion of the first part.

In this manner, it is assured that the cup-shaped element which is permanently connected to the cosmetic sheath, such as by an adhesive or a welded bond does not share in the movement of the articulated connection of the supporting part with the extremity-shaped part.

According to a further aspect of the present invention, the cup-shaped element is formed with a central opening through which the tubular element of the first part passes from the above-mentioned compartment into a space bounded by the cosmetic sheath. The opening may have such dimensions as to permit a relative angular displacement of the tubular element with respect to the extremity-shaped part and to the cup-shaped element.

Especially when the extremity-shaped part is of a synthetic plastic material, it is advantageous to form such extremity-shaped part with a depression which is bounded by a circumferential rim. The cup-shaped element may then be snugly received in the above-mentioned depression, being circumferentially surrounded by the above-mentioned rim. In this event, the rim may have a flat end face, and the cup-shaped element may have a circumferential edge which is flush with the above-mentioned end face of the rim.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DISCUSSION OF THE PREFERRED EMBODIMENTS

Figure 1:
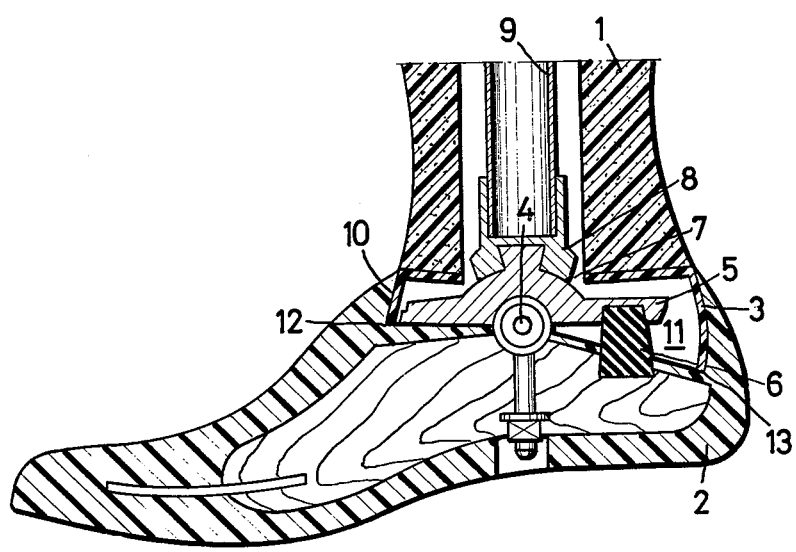
FIG. 1 is a sectional side view of a first embodiment of the present invention.

Referring now to the drawing, and first to FIG. 1 thereof, it may be seen that the prosthetic appliance of the present invention includes a cosmetic sheath which has been designated with the reference numeral 1. An extremity-shaped, such as a foot-shaped, part has been designated in toto with the reference numeral 2 and, as may be ascertained from FIG. 1, it includes a wooden inner core and an outer layer of a synthetic plastic material. However the extremity-shaped part 2 may be made of wood or a synthetic plastic material in its entirety, if so desired, or even of other suitable rigid materials.

The prosthetic appliance further includes a cup-shaped element 3 which is connected in an end-to-end fashion, with an end face of the cosmetic sheath 1. The bond between the cup-shaped element 3 and the cosmetic sheath 1 is advantageously permanent, and is preferably obtained by adhesively or weldingly bonding the end face of the cosmetic sheath 1 to the end face of the cup-shaped element 3. The cup-shaped element 3 bounds a compartment, and a tilting element 5, which is connected to the extremity-shaped part 2 by means of a pivot 4, is accommodated within such compartment. An elastically yieldable bumper member 6 extends between and abuts against the tilting element 5 and the extremity-shaped part 2. The cup-shaped element 3 has a central opening 7 through which a tubular element 9 of a supporting part, of which the tilting element 5 constitutes an end portion, extends from the compartment bounded by the cup-shaped element 3 into a space bounded by the cosmetic sheath 1. The supporting part may further include, as illustrated, a connecting member 8 which connects the tubular element 9 with the tilting element 5.

As may be further seen in FIG. 1, the foot-shaped element 2, which may be made at least partly of a synthetic plastic material, includes a circumferentially complete collar or rim 10 which circumferentially bounds a depression 11 in which the articulated connection of the foot-shaped part 2 with the tilting element 5 is accommodated. The cup-shaped element 3 is preferably snugly or pressfittingly accommodated within the depression 11. The cup-shaped element 3 is preferably made of an elastic material and has an upper edge which is preferably flush with the end face of the rim 10. The cup-shaped element rests on the foot-shaped part 2 at least at two points designated with reference numerals 12 and 13, but preferably there exists a surface contact of the outer surface of the cup-shaped element 3 with the surfaces bounding the depression 11.

The cup-shaped element 3 has such dimensions and particularly such a height that the tilting element 5 is received within the compartment bounded by the cup-shaped element 3 with such a spacing that freedom of angular displacement of the tilting element 5 relative to the cup-shaped element 3, and thus to the extremity-shaped part 2, is assured. It will be appreciated, upon consideration of the drawing and the discussion, that the cosmetic sheath 1 does not share in the angular displacement of the tilting element 5.

Figure 2:
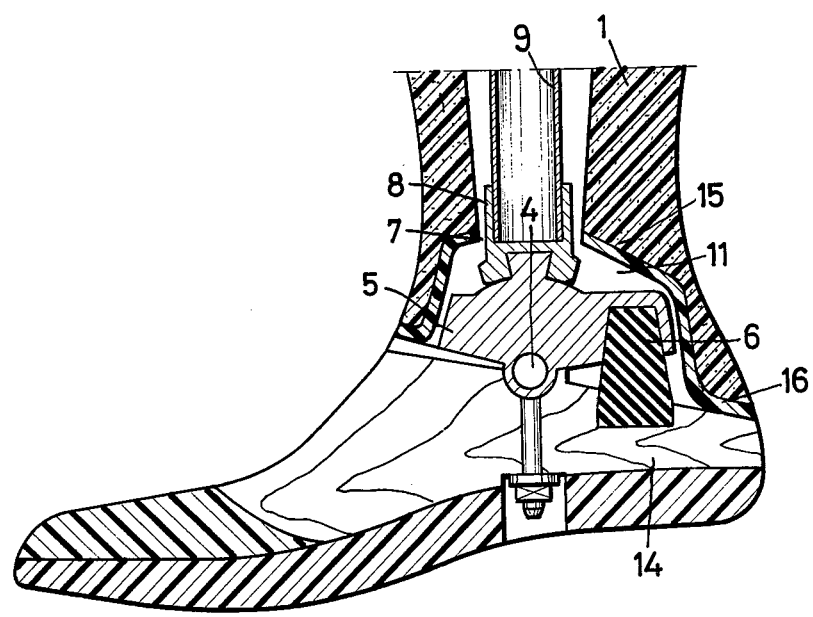
FIG. 2 is a view similar to FIG. 1 but showing a different embodiment of the present invention.

The embodiment of FIG. 2 is in many respects similar to that of FIG. 1 so that the same reference numerals have been used in FIG. 2 to designate parts similar in configuration and function to the parts of FIG. 1. In this embodiment, the foot-shaped part is identified by a reference numeral 14 and is made predominantly or exclusively of wood. The foot-shaped part 14 has, in the region of the tilting element 5, an approximately flat surface, the circumferential rim of FIG. 1 being omitted in this embodiment. The cup-shaped element 15 has a circumferential edge 16 which rests upon the flat surface of the foot-shaped part 14. The adjustment of the position of the cup-shaped element 15 relative to the foot-shaped part 14 is obtained by means of non-illustrated conventional screws or the like. In this embodiment, the tilting element 5 is again received with spacing within the compartment bounded by the cup-shaped element 15, so that the cosmetic sheath 1 again does not participate in the angular displacement of the tilting element 5.

It will be understood that each of the elements described above, or two or more together, may also find a useful application in other types of constructions differing from the types described above.

While the invention has been illustrated and described as embodied in a foot-replacing prosthetic appliance, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. In a prosthetic appliance, a combination comprising an elongated supporting part having an end portion and including a tubular element; an extremity-shaped part articulated to said end portion of said supporting part and having a circumferential rim bounding a depression; a sheath of a resiliently yieldable material surrounding at least a portion of said supporting part; and means for connecting said sheath to said extremity-shaped part, including a cup-shaped element permanently connected to said sheath, snugly received in said depression, and detachably circumferentially held in the latter by said rim, said cup-shaped element bounding a compartment in said depression in which said end portion of said supporting part is received and having an opening through which said tubular element passes from said compartment into a space bounded by said sheath, said opening having such dimensions as to permit said supporting part to tilt relative to said cup-shaped element and to said extremity-shaped part.

2. A combination as defined in claim 1, wherein said extremity-shaped part is at least partly of a rigid material.

3. A combination as defined in claim 2, wherein said rigid material is wood.

4. A combination as defined in claim 2, wherein said rigid material is a synthetic plastic material.

5. A combination as defined in claim 1, wherein said yieldable material is of a foamy consistency.

6. A combination as defined in claim 1, wherein said supporting part further includes a tilting element separate from and rigidly connected to said tubular element and constituting said end portion of said supporting part.

7. A combination as defined in claim 1, wherein said rim has a flat end face; wherein said cup-shaped element has a circumferential edge; and wherein said edge is flush with said end face.

* * * * *